US006400989B1

(12) United States Patent
Eckmiller

(10) Patent No.: US 6,400,989 B1
(45) Date of Patent: Jun. 4, 2002

(54) ADAPTIVE SENSORY-MOTOR ENCODER FOR VISUAL OR ACOUSTIC PROSTHESIS

(75) Inventor: Rolf Eckmiller, Bonn University (DE)

(73) Assignee: Intelligent Implants GmbH, Bonn (DE)

( * ) Notice: Subject to any disclaimer, the term of this patent is extended or adjusted under 35 U.S.C. 154(b) by 0 days.

(21) Appl. No.: 09/367,030

(22) PCT Filed: Feb. 20, 1998

(86) PCT No.: PCT/EP99/00968

§ 371 (c)(1),
(2), (4) Date: May 30, 2000

(87) PCT Pub. No.: WO98/36795

PCT Pub. Date: Aug. 27, 1998

(30) Foreign Application Priority Data

Feb. 21, 1997 (DE) .......................................... 197 07 046

(51) Int. Cl.⁷ ............................................... A61N 1/18
(52) U.S. Cl. ............................... 607/54; 623/4; 623/10; 607/55
(58) Field of Search ................. 607/53–57; 623/4, 623/10

(56) References Cited

U.S. PATENT DOCUMENTS

| 2,215,088 A | 9/1940 | Soss |
|---|---|---|
| 3,766,311 A | 10/1973 | Boll |
| 4,628,933 A | 12/1986 | Michelson |
| 5,109,844 A | 5/1992 | de Juan, Jr. et al. |
| 5,277,886 A | 1/1994 | Young |
| 5,351,314 A | 9/1994 | Vaezi |
| 5,411,540 A | 5/1995 | Edell et al. |
| 5,441,532 A | 8/1995 | Fenn |
| 5,496,369 A | 3/1996 | Howard, III |
| 5,501,703 A | 3/1996 | Holsheimer et al. |
| 5,512,906 A | 4/1996 | Speciale |
| 5,545,219 A | 8/1996 | Kuzma |
| 5,549,658 A | 8/1996 | Shannon et al. |
| 5,569,307 A | 10/1996 | Schulman et al. |
| 5,571,148 A | 11/1996 | Loeb et al. |
| 5,597,381 A | 1/1997 | Rizzo, III |

Primary Examiner—Jeffrey R. Jastrzab
(74) Attorney, Agent, or Firm—Venable, Baetjer, Howard & Civiletti, LLP

(57) ABSTRACT

The invention describes an adaptive, sensory-motor encoder for a visual prosthesis or for an acoustic prosthesis and equipped with a central control unit for signal processing functions, monitoring functions, control functions and external intervention functions as well as with a group of adaptive spatio-temporal filters for the conversion of sensor signals into stimulation impulse sequences, whereby a bi-directional interface is provided for coupling the encoder with an implantable microstructure (2) for stimulation of nerve or glial tissue on the one hand, and on the other hand for function monitoring of brain function.

44 Claims, 5 Drawing Sheets

ADAPTIVE SENSORY-MOTOR ENCODER FOR VISUAL OR ACOUSTIC PROSTHESIS

BACKGROUND OF THE INVENTION

1. Field of the Invention

The present invention concerns an information processing system including an adaptive, sensory-motor encoder for a visual prosthesis or acoustic prosthesis for bi-directional coupling using implanted micro-contacts both for stimulation of neural or glial tissue as well as for the purpose of functional monitoring of brain function.

2. Description of Related Art

A number of attempts have been made to develop vision prostheses for various groups of blind persons by implantation of micro-contacts at the output layer of the retina (RET) or within the visual cortex (VCO) and by coupling these implants with an external signal transmitter (the encoder) in order to elicit functional visual perceptions. For example, encoders for implantable vision prostheses are described in U.S. Pat. No. 5,498,521, U.S. Pat. No. 5,351,314 or WO95/06288; implantable micro-contacts for the retina, visual cortex or auditory system are described in U.S. Pat. No. 5,597,381; U.S. Pat. No. 5,569,307; U.S. Pat. No. 5,549,658; U.S. Pat. No. 5,545,219; U.S. Pat. No. 5,496,369; U.S. Pat. No. 5,411,540; U.S. Pat. No. 2,215,088; U.S. Pat. No. 5,109,844 and U.S. Pat. No. 4,628,933. U.S. Pat. No. 5,277,886, EP 0435559 and U.S. Pat. No. 3,766,311 are concerned with neural networks and the visual system and U.S. Pat. No. 5,571,148, U.S. Pat. No. 5,512,906, U.S. Pat. No. 5,501,703, U.S. Pat. No. 5,441,532, U.S. Pat. No. 5,411,540 are concerned with addressing micro-contacts.

The target groups of the RET projects suffer retinal degenerative disease (for example, retinitis pigmentosa, macular degeneration) whereby the photoreceptor layer has degenerated but at least a portion of the retinal ganglion cells and part of the optic nerve originating there, as well as the central visual system are still functional. As is demonstrated by the publications mentioned above, work is being done on development of a variety of types of implantable micro-contact structures (stimulators), that are applied inside the globus oculi (eyeball) onto the ganglion cell layer of the retina and on the development of wireless signal and energy transfer systems for connection between the external encoder and the implanted stimulator, or generally to the interface.

The inventor has confronted the task of further developing an adaptive encoder for a visual prostheses that is coupled at the retina or to the visual cortex for conversion of image patterns or for acoustic prostheses coupled to the appropriate areas of the neural auditory system for conversion of sound patterns into stimulation signals through adaptive, spatio-temporal filters using receptive field characteristics of the respective sensory neurons (RF filters) addressed and their optimal adjustment by neural networks acting as adaptive function approximators.

The target groups of VCO projects typically no longer have recoverable optic nerve function and therefore require implantation of, for example, comblike micro-contact structures into regions of the visual cortex; that is the occipital cortex, that are directly adjacent to the cranium.

There are also several familiar types of acoustic prostheses (for example, the cochlear implant) using implanted micro-contacts that make possible partial recovery of auditory perception in deaf persons.

The current designs of implant systems do not provide for any information processing of the dynamic image pattern data within the visual system (for example, the retina), from the optical input up to the neural layer contacted by the implanted micro-contacts (for example, the ganglion layer of the retina or the neural layer in the visual cortex). Instead, simple image patterns (for example, lines) are forwarded directly as stimulation signals at the locally distributed micro-contacts without individually adapted information processing as a substitute for that part of the visual system that is to be technologically bridged (for example, the retina). The visual system that has been so rudimentarily and unadaptively stimulated is confronted with the difficult problem of generating visual perceptions, that are sufficiently similar to the image pattern, from the locally and temporally incorrectly processed or coded signal paths. Furthermore, the physiological adjustment of the visual sensitivity (brightness adaptation) over approximately 10 decades and the functional alteration of the receptive field characteristics or features connected with it in technical photosensor systems is not taken into account.

The currently developed implant systems using available technology do not use visual prostheses for the purpose of warning the implant carrier of hazards and reporting technically identified patterns. The same applies to currently developed implant systems for the auditory system.

Because of its ontogenetically established structure and its stabilized structure and function through years of visual perceptual experience prior to the occurrence of blindness, the visual system expects, for example, a particular kind of information processing of the image pattern data by each retinal ganglion cell via the optic nerve. This expectation is neurophysiologically transcribed by the corresponding receptive field features (RF) of the neuron and is very variable, is not fulfilled, inasmuch as, for example, the function of the retina, electrically stimulated by static pre-processing, cannot be individually adjusted for each single, stimulation contact produced by implantation. The same applies to the auditory system.

The collaboration necessary for the normal vision process of the central vision system receiving its inputs from the retina with the respective eye movement system is called the sensory-motor "Active Vision" system.

Such systems for pattern recognition, object tracking, object position recognition, etc. are taken into consideration in conventional applications. The visual system nevertheless requires eye movements for all vision performances and produces not only recognition performances (what?), but very importantly recognition performances (where?) as well as orientation in space, all of which have a very high priority for the visually challenged person who is in the process of partially recovering his ability to see. Triggering of visually induced eye movements, however, in the case of actual stimulation by the use of the implant system, cannot be expected from only a small fraction of the retinal ganglion cells or the cells in the visual cortex. Therefore, the visual system, using the implants that are currently in the development stage and which are based on normal cooperation with eye movements, can perform only unsatisfactory visual perception, if any at all.

In various visually challenged persons there occur, in addition, undesired, non-visually induced eye movements with slow and fast phases, that can significantly impair optimal utilization—and thus the acceptance—of this type of visual prosthesis. If, for example, the encoder with photosensor array is fixed onto the globus oculi, the then desired locus of fixation is constantly shifted by the undesired eye movements. If, on the other hand, the encoder is built into an eyeglass frame, then the visual system will interpret the image pattern with the eye movements that have not been harmonized with the image pattern, as ambiguous visual perceptions, for example, as apparent movement, as is, for example, the case in vertiginous perceptions.

Without the possibility of visually induced, real eye movements and the additional conflict with undesired spontaneous eye movements, visual orientation in space, position identification of various objects relative to the location of one's own body—for example for the intentional grasping of a door knob—using visual prostheses currently in development, which are dependent on head and upper-body movements for the change in direction of vision, are barely possible. The structures to be implanted have a very limited number of micro-contacts. The number of effective usable micro-contacts is even smaller, since only a fraction of the contacts can be positioned by implantation relative to a nerve cell or fiber, so that with the use of individual contacts, or contact pairs, neural action potentials with acceptably low stimulation amplitudes can be triggered. In the cases of current development, there is hardly the opportunity to increase the number of permanently and selectively contacted neurons beyond the quantity accidentally established at implantation. This is one reason for the only minimum visual perception quality that can be expected. The same applies to implant systems in the auditory system.

SUMMARY OF THE INVENTION

The currently developed micro-contacts and signal and energy transfer systems for implantation of visual prostheses function unidirectionally from the external encoder to the implanted stimulator and therefore offer no opportunity for ongoing monitoring of the neural impulse activity of the stimulated neurons. Thus, the stimulation pulse frequency cannot be adjusted to the spontaneous activity of the neurons. Furthermore, the triggering of neurobiological impulses by stimulation (excitatory) pulse cannot be directly monitored. Furthermore, there is no sure opportunity for impulse monitoring for a possible temporal tuning and synchronization of the impulse sequence of several neurons. The same applies to the auditory system.

The task of the present invention is to eliminate these disadvantages and to provide an adaptive sensory-motor encoder.

This problem is solved by a device having the characteristics described in this disclosure.

Because the encoder operates in bi-directional coupling with implanted micro-contacts on the retina or on the visual cortex after—preferably with the aid of neural networks in carried out in dialogue with the implant carrier—functional tuning as individually required, various visual recognition, tracking, and location identification tasks as well as reporting of hazards and technically identified patterns can be performed by technical image pattern shifting and simulated eye movements, the number of selectively reachable stimulation sites functionally increased, and the neural activity of neurons to be stimulated can be monitored. Furthermore, the encoder functions of brightness adaptation and composition of a visual operating range from excerpts of a large function range described here can be done.

With implementation of an acoustic prosthesis, the adaptive encoder can provide corresponding services in the auditory area.

In the case of the preferred design form of the encoder for a visual prosthesis, a digital signal processor (DSP), for example, the Texas Instruments model C80, is integrated with a photosensor array with optics as the light pattern receiver, a pre-processing module for visual patterns, an impulse signal emitter and receiver for bi-directional communication with the implanted structure, several signal interfaces for communication with the evaluation input unit, the head movement sensor, the eye movement sensor, the perception, warning, and recognition system, pattern and object reporting system and the external monitoring and control system integrated into an eyeglass frame. The various adaptive information processing functions, particularly for RF filters, dialogue module, pattern recognition, and Active Vision functions are provided in the DSP with a central control unit. The user receives, on the one hand, signals as stimulation impulses or receives sensory perceptions from the encoder and transmits, on the other hand, signals regarding head and eye movements as well as the evaluation entry and neural activity to the encoder. Because of a bi-directional wireless signal and energy transfer, the encoder can be installed in an eyeglass frame, attached to a contact lens on the eye, placed on the body, or located at a body-remote site. Finally, the spatio-temporal functional range of the RF filter used as a retinal encoder includes, for example, the receptive field characteristics of retinal ganglion cells or other intra-retinal neuron classes of the primate retina. The same applies to the preferred designs of the encoder in coupling with the neurons of the visual cortex or in the case of an acoustic prosthesis for coupling with neurons of the auditory system.

A suitable form of a procedure for adjustment or setting the RF filter of the encoder in the dialogue with the user is illustrated schematically in FIG. 1 and FIG. 2. The RF filters are executed as a spatio-temporal filters whose spatial and temporal functional parameters are modified in a sufficiently large function range for approximation of the receptive field characteristics of visual neurons, namely, by externally accessible parameter exchange points placed at appropriate positions in the filter algorithms. A human being communicates, as a normal-sighted person or implant carrier in a perception-based dialogue with the encoder, the perception comparisons between the desired and the actual patterns, for example, through an evaluation input unit composed of a line of several dip switches (see FIG. 2), to a technical neural network with non-monitored adaptation rules. The neural network then establishes the next parameter vector for the RF filter as well as the next desired pattern, with the goal of reduction of the perceived pattern difference in the next dialogue step. In the search for optimum parameter vectors for the RF filter, parameter vectors that result in a certain visual perception for a given light pattern presented and appropriately subjectively interpreted can be produced in the dialogue module of a neural network using non-monitored adaptation. Alternatively, in the dialogue module, another parameter-setting system can produce sequences of parameter vectors for virtual movement in the functional space of the RF filter, for example, as continuous trajectories depending on the type of scanning or sweep, as rule-less sequences or as sequences of neurophysiological especially typical filter functions, and the user, during this sequence running in an appropriate timing scheme, occasionally reports "sensible" perceptions resulting from the interaction of the given light pattern, the series connected pre-processing module, the series connected RF filter and the part of the central visual system coupled via the appropriate micro-contact. Then, a more precise perception-based parameter optimization is carried out in the so-determined range of the filter function space. A suitable form of the dialogue-based setting of the RF filter of the encoder of an acoustical prosthesis is done in similar fashion.

In the generation of asynchronous impulse sequences, the output signals of the particular RF filter are, through suitable conversion algorithms of the quasi-continuous time functions of the RF filter, converted to asynchronous impulse sequences suitable to the activity of visual neurons in the primate visual system, and impulse sequences-time courses, as well as onset times of a particular impulse, are adjusted through variable time delay elements during the dialogue phase. A suitable form of the vision system model for the perception comparison in normal-sighted persons is found in the fact that for a series of RF filters, individually or as a group, the respective appropriate inverse representation is provided and thus parameter vectors are established as precise. Through sequential switching with the encoder an actual image is produced on the right screen with considerable similarity to the desired pattern. At the start of the dialogue the parameter vectors of the RF filter are set to random start values so that initially there is a clear difference between the patterns, but in the course of the dialogue with non-monitored adaptation becomes consistently less.

The functional adaptation of the RF filters for the implant carrier in the perception-based dialogue occurs in contrast with the functional adaptation for normal-sighted persons in that the actual perception is not accessible on a monitor but is only internally accessible to the implant carrier and that the desired perception is communicated to the implant carrier is, for example, as speech information or as a tactile contact pattern on the skin. When used in acoustic prostheses a similar situation exists wherein, instead of the inaccessible auditory organ, for example, along with the tactile sense the available vision sense can be employed to communicate the desired perception.

The temporal coupling of the asynchronous impulse sequences produced by several RF filters of the encoder for triggering of neural impulses occurs in that the transmission time points of the individual impulse signals are varied by controllable time delay elements such that there is a temporal coupling resulting in precisely synchronous occurrence so that the variation of the time delay is controlled by the implant carrier, results in the dialogue as perception-based event by way of a neural network or is controlled externally, that the selection of the impulse groups to be coupled temporally can be taken into consideration [ber ücksichtigt] both by the impulses coming from the RF filter as well as the impulses recorded in the interface, and that in view of the very different momentary impulse rates of the various RF filters suitable criteria are established for the participation of individual impulses in the impulse groups to be coupled.

For the purpose of functional enhancement of the number and of the selectively reachable stimulation sites with a given number of stationary micro-contact implants, the impulse signals from a given RF filter are guided to several, neighboring micro-contacts.

The characteristic time courses of the electromagnetic field in the area of the neurons to be stimulated—based on the encoder commands and set exactly for each micro-contact and decoded stimulation time functions corresponding in the interface with respect to current amplitude, polarity and phase length—have the effect that these stimulation signals that are tuned to each other by superpositioning, trigger local and temporally selective neural impulse excitations a field strengths at several micro-contacts. The selective simulation occurs through appropriate variation of the superimposed stimulation signals and can be rapidly changed. The corresponding variation of diverse parameters of the reciprocally-tuned stimulation signals in the perception-based dialogue with the implant carrier occur via the neural network, or other signal variation processes at the adjacent electrodes, such as, for example, a continuous, sweeplike automatic shift of the functions parameters of the stimulation impulses that are superimposed upon the nerve tissue and used in the determination of as many as possible stimulation sites that will result in neural excitation, In addition, through the comparison of recorded neural impulses with the stimulation signals, the optimization of the stimulation time functions with respect to intended single-cell selectivity and permanent biocompatibility is improved.

For the purpose of simulation of eye movements for utilization of the encoder in a vision prosthesis, an image pattern shift is done electronically in the input layer of the encoder by optical variation of the direction of vision, for example, with the aid of a moving mirror or by movement of the photosensors for simulation of eye movements. Head movements and eye movements are detected by microminiaturized movement detectors operating multidimensionally, and neural or conventional movement control is provided by using the detected head and eye movement signals and the image pattern shift. Rapid and slow eye movements for the tasks of pattern recognition, rapid peripheral scanning or eye tracking movements are produced, and by the appropriate eye movement sequences with fast and slow phases optimal adaptation of the sensory data flow results at the responsive central vision system. With respect to the production of eye tracking movements, there is a suitable design form in that an adaptive neural predictor picks up the initially unknown movement time function of the object to be followed from the position and movement errors of its projection on the photosensor array, and using an appropriate non-linear adaptive prediction algorithm with consideration of the analyzed frequency segments of the object movement, an object tracking-time function with minimal delay or even with minimal lead is generated internally with rapidly increasing reliability and, in the case of temporary disappearance of the object being tracked, for example, similar to the situation in which the eye tracking movement system in primates produces a movement time function, which, depending on the nature of the object, results in a continuation of the tracking on reappearance of the object, which has moved relative to the sensor array, with minimal positional and movement error.

For the purpose of detection of eye and head movements and for compensation of undesired eye movements fast and slow eye movements are produced by using the detected head and eye movement signals and the simulated eye movements [created] with the help of a neural or conventional movement control or guidance. With the aid of the control loop undesired eye movements are compensated following an appropriate period of adaptation and so that an adequately satisfactory simulation of the vestibular-ocular reflex (that is, the automatic reflex stabilization of the direction of vision in space by eye movements that counteract head movements that may occur) is produced from the head movement detector, image pattern shift and a neural network in a control loop optimized in the period of adaptation, allows positional stabilization of the image pattern, in the presence of natural head and upper-body movements, by corresponding compensatory eye movements.

Simulated eye movements and compensatory eye movements are available as separately selected programs. The individual movement and shift modes can be selected as separate or combination programs, allocated to automatic operation or established externally.

The implant carrier can select the desired "Active Vision" functions, such as looking around or object tracking, by means of a portable command input device; for example, a handheld device with keypad.

Ongoing communication to the implant carrier of the current position of objects picked up visually or acoustically in space consists of the encoder's assessment of the object's position by evaluation of image patterns or sound patterns, eye and head movements using an appropriate, portable signal transmitter reported to the appropriate sensory organ; for example to the tactile sense, and that the encoder by means of an internal pattern recognition program, in particular in conjunction with automatically occurring eye movements, warns the implant carrier of obstacles or hazards and reports type and position of technically identified patterns or objects.

A monitoring system for a partially sensory-motor autonomously operating implanted structure of the encoder consists in the implanted micro-contacts being used both for the stimulation and for recording of neural impulses, such that the recorded impulses and other physical or chemical signals from the implanted structure are reported to the encoder by the appropriate pre-amplifiers and optical or electromagnetic transmitters and that, once there, the recorded neural signals are further processed for the various purposes of the encoder functions.

For the purpose of technical adaptation of the brightness-operating range from a, for example, via a photosensor array function range extending over six to ten brightness levels, that includes both large portions of the scotoptic range of dark adaptation as well as the photoptic range of bright adaptation, a rapidly adjustable electronic display on an internal operating range for the encoder, relative to size and adaptation brightness, is adjusted perception-based, automatically selected or by the user. By doing so, visual scenes of very different brightness are compensated into the current operating range and thus contrast optimization and avoidance of glare is achieved. Furthermore, an advantageous design is inherent here in that the RF filter functions; for example, corresponding neurobiologically familiar processes can be adjusted using the adaptation range.

In a suitable form, a pre-processing module is provided that is equipped for recognition of characteristic patterns and/or for data reduction. When this is done the pre-processing module can recognize bright and dark image areas of differing luminance, separate them from one another, and integrate them to an overall image with the respective regional optimal contrast; likewise image areas lying proximately or remotely separate from one another can be optimized with respect to sharpness adjustment and then reintegrated as an overall image and, finally, characteristic patterns like, for example, warning signs, can be emphasized. This pre-processing can be used to improve the image presentation, but it can be used also for the production of warnings and for data reduction in the communications channel between the camera and the encoder.

It is of further advantage if in the course of a process the adaptation of the accommodation initially, for example, in the foreground, is selectively adjusted, these ranges are stored, and then secondary ranges of the visual field are adjusted sharp as images; for example, the background of a visual field. The initial ranges that now become flat (i.e., unsharp) are faded out of the second image pattern and replaced by the first stored, sharp ranges. By doing this, a depth of definition is produced that is unattainable in the scope of geometric optics. With the cyclically repetitive course of this process step and corresponding image balancing the user remains unaware of the process so that even in minimal light intensity and long focal distances the appropriate optics an image of great definition is apparently obtained.

The adaptive pre-processing module processes the image pattern or sound pattern by neural networks or in pre-processing algorithms for a visual prosthesis accessible in the hardware particularly with respect to color, contrast, edge detection, segmentation, and figure-to-background separation or, in the case of an acoustic prosthesis, for example, with respect to suppression of interference noise, undesired formants and separation of individual sound sources in such a manner that the subsequent RF filter array is considerably simplified and contains imgage patters or sound patterns formed in part from the pattern area in a characteristic or properties area, that is as well adapted as possible to the part of the visual system or auditory system contacted. The various pre-processing functions are set directly by the user or selected by a perception-based dialogue or set automatically. The image simplified in this process and communicated to the retinal encoder is advantageous for figure recognition even in the case of a limited number of visual system neurons contacted. In the pre-processing for acoustic prostheses, corresponding benefits result if complex sound patterns are prepared in the course of pre-processing for speech recognition.

DETAILED DESCRIPTION OF THE PREFERRED EMBODIMENT

Figure 1:
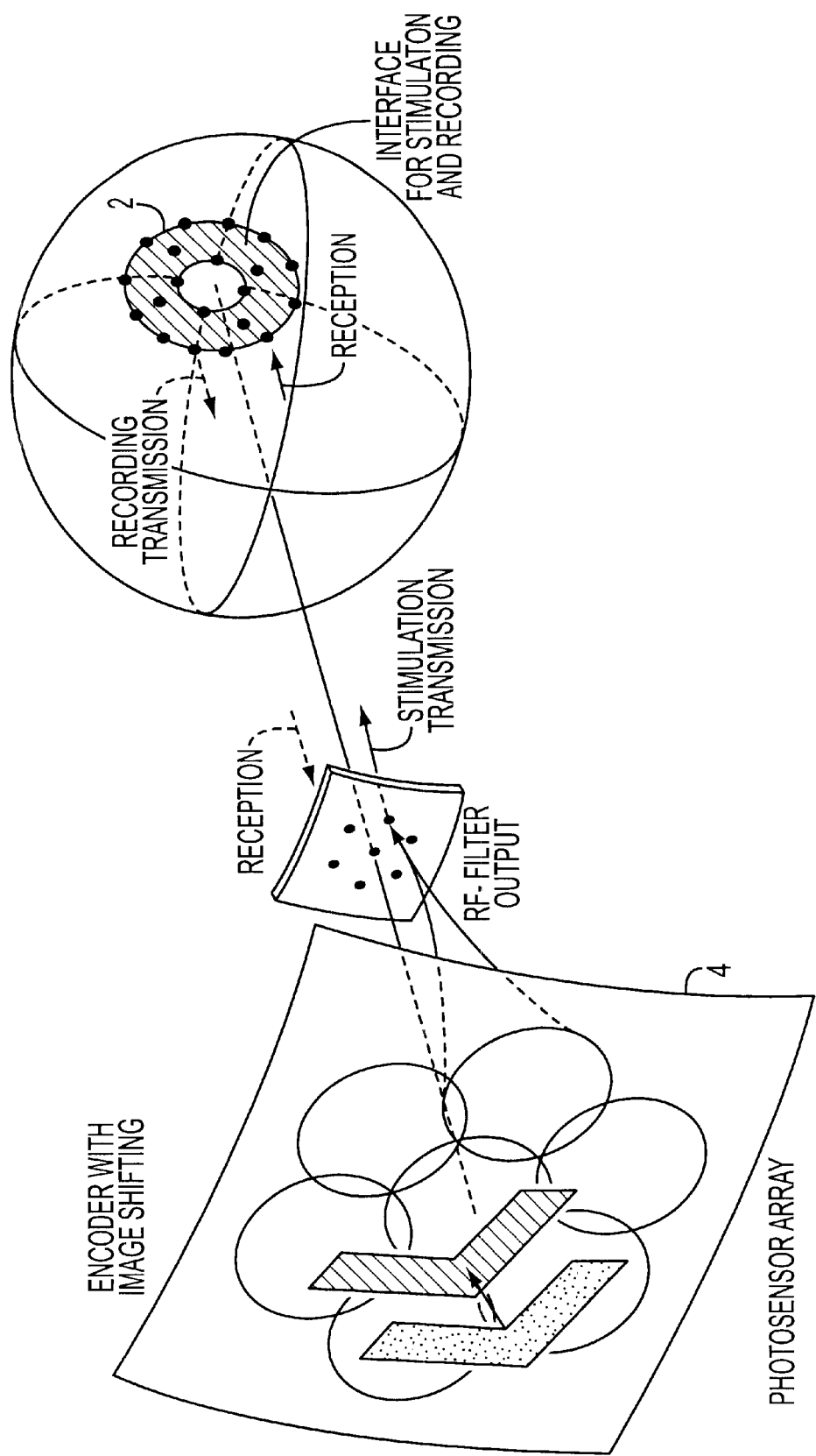
FIG. 1 illustrates a visual prosthesis using the example of a retinal implant.

FIG. 1 shows schematically a visual prosthesis using the example of a retinal implant with an adaptive, sensory-motor encoder with image shifting mounted in an eye glass frame; a interface, implanted in the eye in proximity to the ganglion cell layer for stimulation and recording as a micro-contact structure (2) with accessory electronics and a bi-directional, wireless signal and energy transfer system between the encoder and the interface. The individual spatio-temporal filters (RF filters) of the encoder with each approximately round cutouts of the photosensor array (4) in the input layer (left) and the related signal outputs in the output layer (middle) represent typical receptive field characteristics, for example, of ganglion cells of the primate retina, or of neurons in the visual cortex and are individually adjustable as to function by parameter vectors. The interface receives not only stimulation signals from the encoder but also sends recorded neural impulse signals to the recorder. The components that are additionally associated with the encoder such as, for example, the central control unit or the pre-processing module connected upstream of the RF filters are not shown in FIG. 1.

Figure 2:
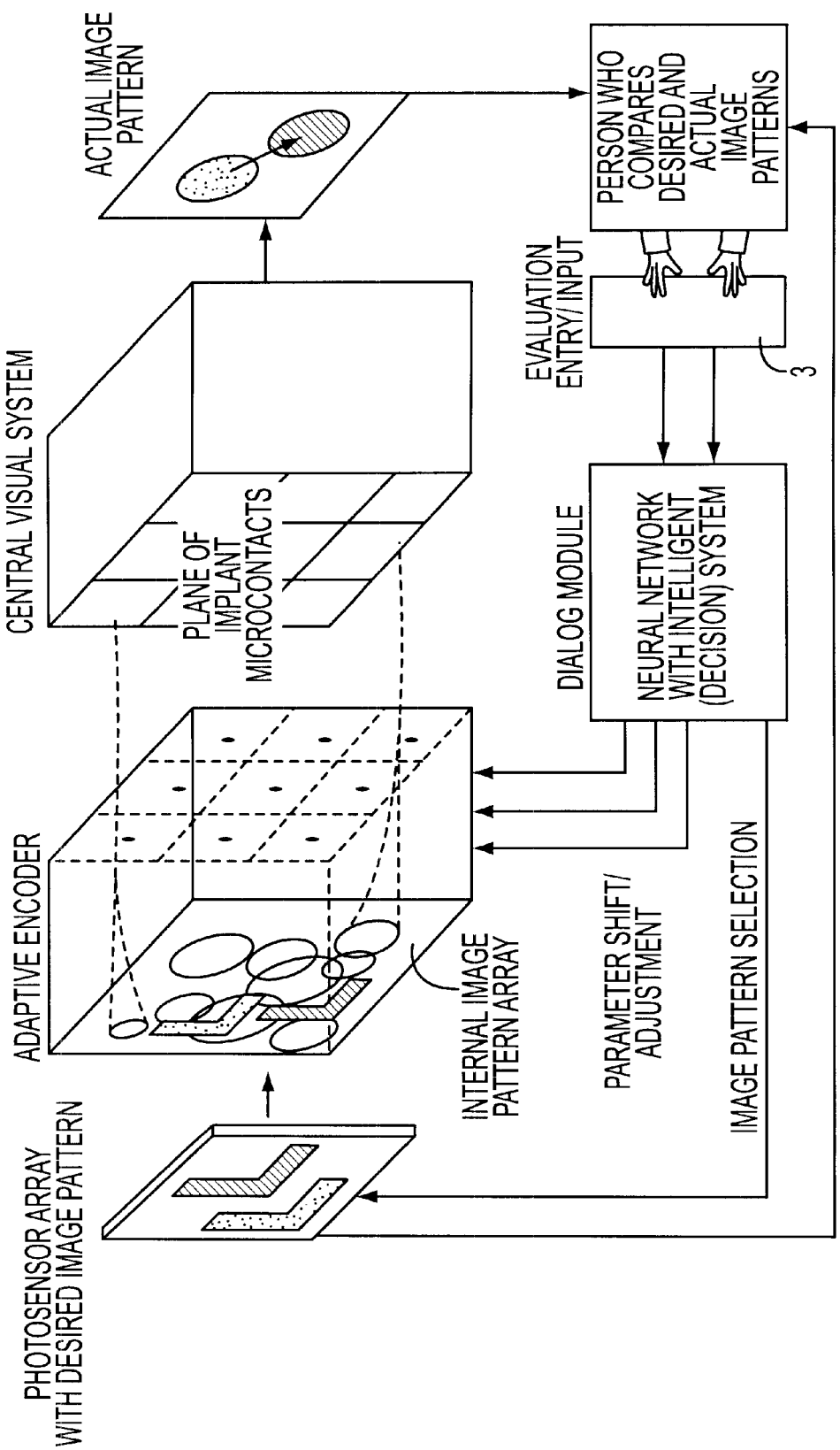
FIG. 2 illustrates an adaptive encoder with dialogue system.

FIG. 2 shows the layout of the encoder (1) with dialogue system in a coupling with the central visual system, either as a model (implementation in a normal-sighted person), or as an actual system from the level of the implanted micro-contacts up to visual perception (implementation in the implant carrier). The angle as exemplar image pattern on the photosensor array (left) represents at the same time a desired pattern on the monitor, which moves upwards to the right on the connecting internal image pattern array that is done electronically in the encoder, the angle in the example moves from another starting position in another direction, in order to indicate the function of a technical image shift. The screen to the right shows the appropriate actual image pattern and represents either a second monitor (normal-sighted person), or a virtual projection of the visual perception area (implant carrier). The elliptical disc moving from upper left to downward right represents the corresponding perceived actual image pattern. The man (lower right) articulates his subjective evaluation of the comparison of the desired and actual patterns over a multichannel evaluation input. The dialogue module as neural network with a decision system (below) forms the output signals of the evaluation input on a parameter vector for adjustment of the RF filter. With replacement of image, patterns with sound patterns and the visual system with the auditory system FIG. 1 applies correspondingly to the use of encoders for acoustic prostheses.

Figure 3:
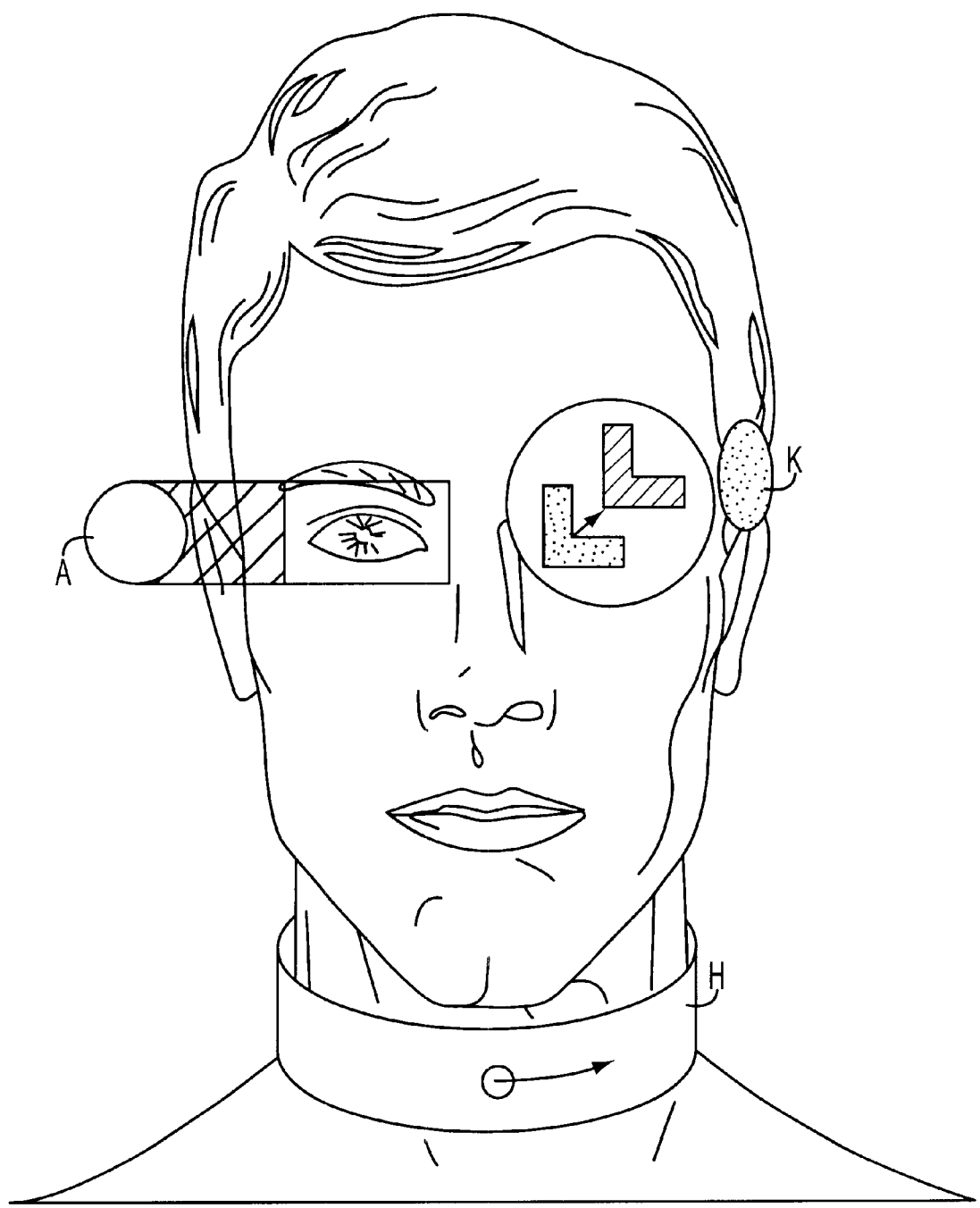
FIG. 3 illustrates a drawing of the head movement and eye movement detectors, the retina encoder anterior to the eye and a neck collar for tactile response of object position.

FIG. 3 shows schematically a suitable design form of the encoder with respect to the positioning of a multidimensionally functioning head movement sensor (K) above the ear, a multidimensionally functioning eye movement sensor (A) and the encoder that has been integrated into an eye glass frame with indicated moved image pattern. A throat collar (H) for the production of local tactile sensations, for example by vibration it provides the user with information regarding the location of an object relative to the user. If an object lying in front of him wanders to the left out of the field of vision, then the vibration area produced on the throat also moves to the left, as indicated in FIG. 3.

Figure 4:
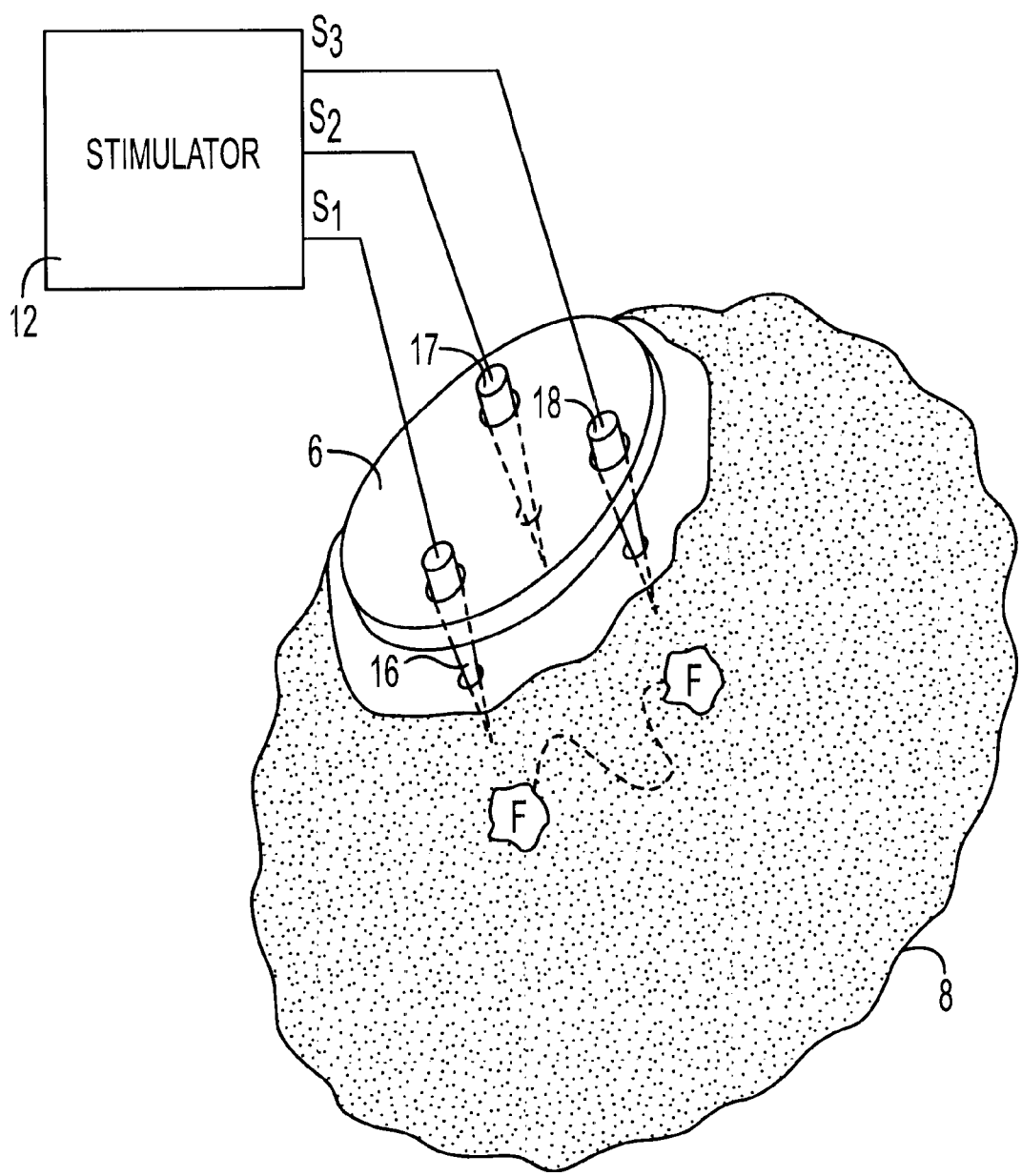
FIG. 4 illustrates a schematic illustration of an implanted micro-contact structure for stimulation of nerve tissue not contacted directly.

FIG. 4 shows an illustrated example of micro-contacts (6) that impinge on nerve tissue (8). In the present example three micro-contacts (16, 17, 18) are implanted in the nerve tissue (8) and there positioned more or less randomly close to certain nerve cells. The micro-contact structure (6, 16, 17, 18) is uniformly essentially coarser than the matrix of the nerve cells (8). Micro-contacts (16, 17, 18) are supplied with Signals (S1, S2 and S3) by way of the stimulator (12).

In order to created targeted neural excitation, a stimulation focus, for example (F), must be reached that cannot be directly affected by a micro-contact. The stimulation focus (F), however, can be reached if the signals (S1, S2, S3) are passed to the electrodes (16, 17, 18) using different strengths, time course and, above all, time spacing. The overlap or superimposition of the signals in the area of the intended stimulation focus (F) exceeds the excitation threshold of individual or a few nerve cells, while the addition of the signal flows in the rest of the area of the nervous tissue remain below the excitation threshold.

By changing the temporal sequence and of the temporal signal flow of the various signals tuned to each other the stimulation focus (F) can also be shifted to (F'). For the pre-compensation of these stimulation functions that attain a stimulation focus that is not in direct connection with an electrode, an adaptive process is required. Since it is not precisely known which stimulation focus (F) an (F') for a particular neural stimulation must be addressed, the adaptive sensory-motor control unit can offer only a particular signal pattern that the implant carrier then assesses by way of a sensory perception or another sensor data evaluation. A second signal pattern that has been changed in comparison to the first one, is then also subsequently assessed as to whether it attains the targeted neural excitation or not. The user needs only say whether the later signal pattern is better or worse than the preceding one. Using this control mechanism of a neural network an optimal signal time function for the electrodes (16, 17, 18) for stimulation of the stimulation focus (F) is determined in the course of the control process.

Figure 5:
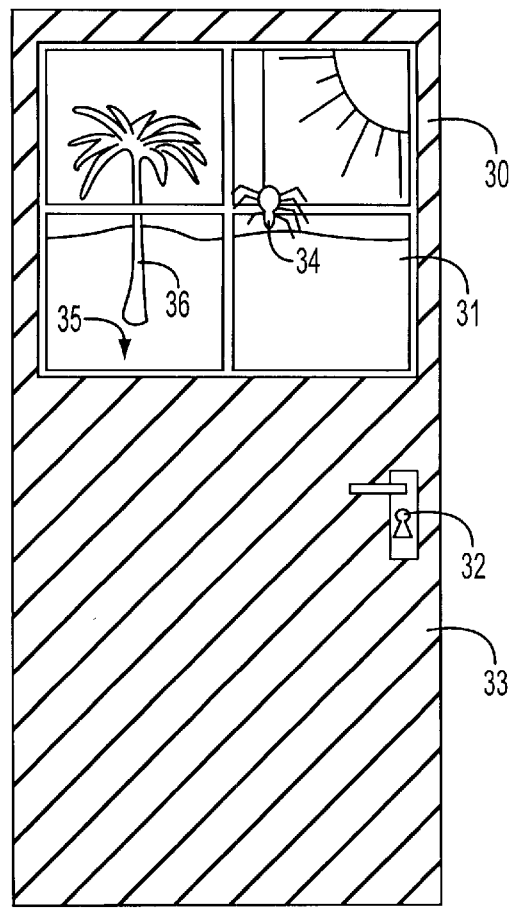
FIG. 5 illustrates a scene with very different brightness ranges and areas of different focal distance.

FIG. 5 shows a scene perceived under practical conditions by the photosensors in which a patio door (30) is observed from inside a room. The door (30) exhibits a window (31), a keyhole (32) and a door panel (33). In front of the door dangles a spider (34) and through the window (31) a beach scene (35) is visible.

The illumination differences in this scene lie between approximately $10^{-1}$ cd/m$^2$ in the area of the door latch to $10^0$ cd/m$^2$ in the area of the spider and $10^1$ cd/m$^2$ in the area of the door panel on up to $10^4$–$10^5$ cd/m$^2$ in the outdoors area. Such brightness differences are not simultaneously visible using conventional cameras and otherwise even with the human eye. The brightness adjustment occurs always only in the currently observed area.

Figure 6:
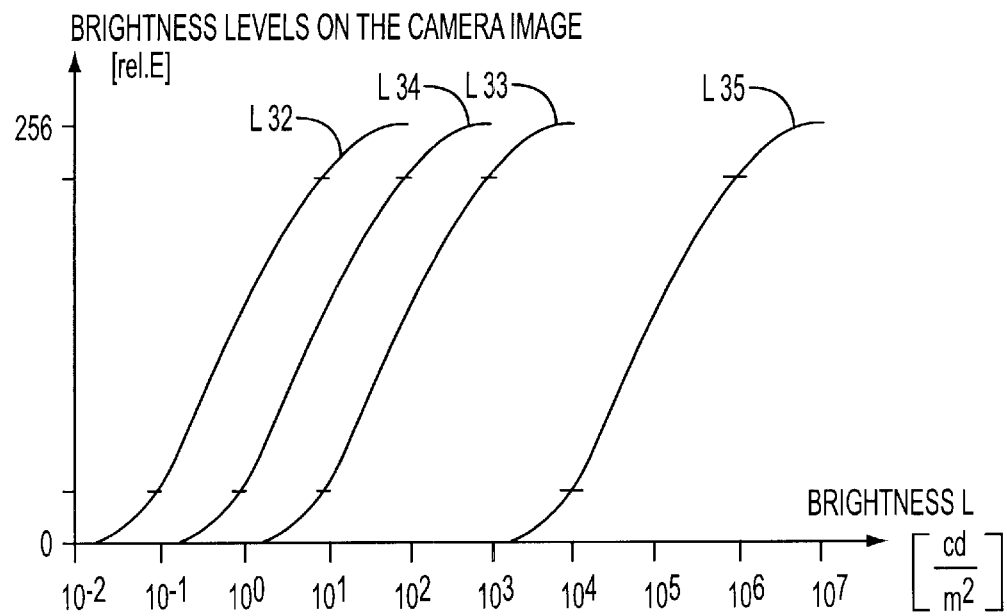
FIG. 6 illustrates the course of brightness stages in the camera image for four different image areas from FIG. 5.

FIG. 6 shows in diagrammatic form how the pre-processing module of the camera (1), because of its pattern recognition functions, delimits the individual areas from one another and converts them using different functions in the brightness layers of the camera imaging. On the x-axis the brightness (i.e., luminance) is represented in cd/m$^2$ over a total of 9 decades, just as they occur in the actual picture in FIG. 5. The y-axis shows the 256 relative units of the brightness information, as attributed to the image representation by the camera or its pre-processing module, 256 units corresponding to a brightness modulation of 8 bits.

An initial brightness curve L32 shows the area of the brightness of the door latch (32), illustrated on the 256 relative brightness levels of the camera imaging. Corresponding brightness curves L33 for the door panel (33), L34 for the spider (34) and L35 for the outdoors area (35) are likewise illustrated.

The pre-processing module recognizes in the detailed imaging different and delimited from one another with sharp contours areas with the four different brightness areas. These areas are constructively separated from one another and each transposed with optimal resolution to the 256 brightness levels of the camera imaging. In the result the scene is shown to the observer as an image in FIG. 5 in which the image areas (32, 33, 34) are illustrated with equal brightness and with the corresponding structuring in the various brightness levels. Such an illustration can be unusual but it offers a richness of detail in various regions that can not be simultaneously illustrated with the human eye or with conventional camera systems.

The illustration in FIG. 5 also shows objects at various distances. Thus, for example, the objects (32, 33 and 34) are at a distance of 2 m from the observer, whereas the palm (36) in the outdoors area (35) can be at a distance of 40 m. Using conventional camera objectives it is generally not possible to simultaneously present both objects (34 and 35) with the same sharpness. The available definition ranges are inadequate to accomplish this.

Using the pre-processing module the adaptive sensory-motor encoder can initially put the remote area (35) into definition and recognize and store the contour-defined delimited regions (the palm) there. Then a second range (i.e. distance) can be selected in which the spider (34) is set up sharply defined, whereby the area (35) becomes unsharp i.e. (blurred). The pre-processing module can recognize this condition and instead of the blurred region (35) will incorporate the previously determined and captured sharp image unit constructively into the image focused at short distance. This sequence can be cyclically repeated in a kind of focus scanning so that from different focal distances sharp areas are continuously determined, captured and incorporated into the overall sharp image. The definition that is virtually attainable in this way is many times better than that of a normal optical system. With adequate frequency of reiteration of the process the image produced can be distinguished by the use only by the particular definition.

According to the invention an encoder is recommended that optimizes the diverse functions by neural networks in dialogue with the implant carrier, in which various functional modes can be selected and the positions of objects picked up can be used and which warns of obstacles, reports technical recognition of patterns as well as functionally increases the number of selectively addressable stimulation sites and monitors the neural activity of individual neurons. The implanted structure can operate almost with sensory-motor autonomy by using suitable sensory and motor components as well as an adaptive control system.

Advantageous designs and variations of the invention are discernable.

The adaptive encoder is characterized in comparison to the conventional visual prosthesis systems by a number of essential advantages. Firstly an encoder is recommended here that is pre-trained by normal-sighted persons and then can be individually adapted by the implant carrier to his functional requirements. For the first time, an encoder is disclosed here that provides eye movement functions as well as compensation of undesired eye movements. Furthermore, for the first time an encoder is disclosed that functionally increases the number of selectively reachable stimulation sites and that can later be adapted to new stimulation conditions. Further, for the first time an encoder is disclosed, that functions bidirectionally; thus, along with the stimulation functions it allows also monitoring and evaluation of the neural activity of the neurons to be stimulated. Corresponding advantages result with the utilization of the adaptive encoder versus the previously developed auditory prosthesis systems.

The adaptability of the imaging functions of the individually adjustable spatio-temporal filters of the encoder using receptive field properties (RF filters) in the entire neurophysiological relevant functional range will be assured in conjunction with neural networks or other parameter setting processes when used for visual or acoustic prostheses.

The individual imaging functions of the individual RF filters ascertained in perception-based dialogue are sufficiently similar to the receptive field properties expected by the visual system; thus they adapt to the function of the visual system created by the tandem connection of encoder and coupled central vision system. This means on the one hand that the spatio-temporal function range prepared by the RF filters incorporates the neurophysiologically relevant function range and, on the other hand, that the RF filters permits, with the aid of a neural network, a continuous movement in the function range with suitable adjustment procedures. The same applies with use of the encoder in acoustic prostheses.

Already in its use in normal-sighted persons a reasonable default setting of the RF filter has been undertaken using corresponding neurophysiological data on the function of the visual system or the auditory systems of primates. In addition, the dialogue process is being tested using the associated components under realistic conditions by stimulation of the perception process. The same applies with use of the encoder in acoustic prostheses.

The RF filters associated with the individual micro-contacts are individually tuned to optimal visual or auditory perception quality in the dialogue between the encoder and the implant carrier.

In contrast with an encoder with static pre-processing; that is, one without the opportunity for individual pre-programming, the individual RF filters are adjusted as separate encoder channels on the basis of the single relevant criterion; namely the visual or auditory perception targeted. Subsequent function changes; for example, as a result of the relocation of micro-contacts, or of changes in the functional parts of the central visual system can be compensated in the entire perception process by appropriate adaptation of the RF filter functions. An advantage of tuning the RF filters function in the dialogue with the implant carrier consists in the consideration of aspects of function that only the implant carrier can bring in and then only in implicit form by subjective evaluation of his visual perceptions and their implementation in encoder adjustment in the optimization process. The same applies to an acoustic prosthesis.

The asynchronous impulse sequences of the individual RF filter outputs of the currently functionally separate encoder channels are tuned to one another as stimulation signals for selective stimulation sites in the dialogue with the implant carrier in consideration of the recorded neural impulses.

Because the temporal coupling or synchronization of the neural impulses of several neurons for neurobiological signal coding in sensory systems is co-employed, this technically (also by evaluation of the recorded neural activity of neurons to be stimulated) effected, temporal coupling brings with it the advantage of enhancement of the quality of the visual perception.

The number of selectively reachable stimulation sites and their definition (separation sharpness) in the case of a fixed number of implanted micro-contacts is functionally increased.

With a given relatively small number of implanted and permanently functional micro-contacts, whose position relative to the neurons can not be modified, it is of considerable advantage, functionally speaking; that is, by production of suitable signals, to increase the number of selectively reachable stimulation sites or neurons and thus at the same time the number of separately accessible encoder channels with a sufficient reserve in RF filters. This effects an improvement of the visual perception quality.

The detection of eye and head movements has the advantage of determination of the current position of visual objects in space. Furthermore, there is an advantage in that undesired actual eye movements can be compensated by appropriate simulated eye movements and, further, suppress visual perception conflicts such as, for example, apparent movements or vertigo.

The production of the individual movement functions as programs that can be selected as separate or combined programs and has the advantage that the implant carrier himself can select the programs depending on his uses for the visual perception quality, instead of being subject to an automatic function. Nevertheless the choice can be made between automatic and option operation.

It is very important to the implant carrier to be able to perceive the current position of a perceived visual or auditory object in order to be able to accordingly correct his orientation in space and, if necessary, his activities. Furthermore, it is of considerable benefit that the implant carrier is warned automatically of obstacles or hazards and the technical recognition of patterns or objects is reported in support of orientation in space.

With the encoder a direct connection to a part of the nervous system is established that is already spontaneously active. Thus, neural impulses from individual neurons are generated without technical stimulation. Monitoring of the neural activity of individual neurons to be stimulated is of considerable advantage for optimum adaptation of the stimulation impulse sequences to the respective spontaneous activity, for precise determination of the stimulation parameters for assured and simultaneous biologically compatible conversion of stimulation impulses into neural impulses as well as for improved optimization of the temporal tuning and synchronization of the neural activities of several neurons.

With technical adaptation of the operating range it is possible to adapt, in the bright-adapted or dark-adapted brightness range, the function to the image pattern or the sound pattern, to accordingly vary the spatio-temporal filter parameters, or to technically compose a operating range that, for example, consists of partial areas of the larger photo-sensor function range that are separated from one another's by decades.

Pre-processing of incoming image patterns, particularly with respect to rapid selection and change opportunities of the respective pre-processing function is made possible.

With the pre-processing module connected the function of an encoder consisting of only a limited number of RF filters is facilitated by the essential simplification of the image pattern or sound pattern and accordingly the perception quality is improved.

What is claimed is:

1. A visual or acoustic prosthesis comprising:
   an adaptive sensory-motor encoder, comprising:
   a central control unit for performing signal processing functions, monitoring functions, control functions, and external pick-up functions, the central control unit including a group of adaptive spatio-temporal filters for converting sensory signals into stimulation pulse sequences;
   an implantable microstructure for providing stimulation to nerve or glial tissue and for functional monitoring of neural functions; and
   a bi-directional interface coupling the encoder to the microstructure, through which at least one of stimulation and control signals are provided to the microstructure and monitoring signals are provided to the encoder.

2. The prosthesis according to claim 1, wherein control unit includes in a perception-based dialog process receptive field (RF) filters, said RF filters comprising adjustable spatio-temporal filters with receptive field properties.

3. The prosthesis according to claim 2, wherein the RF filters are associated with time delay elements for a relative temporal sequence of impulse sequences produced.

4. The prosthesis according to claim 2, wherein a monitor is provided that displays imaging functions produced by the RF filters at least approximately inverted and optically or acoustically.

5. The prosthesis according to claim 1, further comprising:
   a simulated eye movement system, including head and eye movement detectors.

6. The prosthesis according to claim 1, wherein said implantable microstructure comprises:
   a device for application of an active substance, the device being controlled by said central control unit;
   wherein the implantable microstructure records and transmits neural activity, in the form of said monitoring signals, to a monitoring system of said central control unit.

7. The prosthesis according to claim 1, wherein said central control unit further comprises:
   an adaptive pre-programming module, for simplification of image or sound patterns.

8. The prosthesis according to claim 1, further comprising:
   a portable signal transmitter for relaying a position of an object in space, determined by the encoder, to an appropriate sensory organ.

9. The prosthesis according to claim 1, wherein said central control unit includes at least one pattern recognition program.

10. The prosthesis according to claim 1, further comprising:
    feedback apparatus for training said encoder.

11. The prosthesis according to claim 10, wherein said feedback apparatus comprises:
    means for inputting evaluation inputs, the evaluation inputs representing a comparison between an original stimulus and a detected stimulus; and
    a dialog module, the dialog module receiving the evaluation inputs and providing feedback to the encoder for purposes of adaptation.

12. The prosthesis according to claim 11, wherein said dialog module comprises a neural network.

13. An adaptive sensory-motor encoder for use in a visual or acoustic prosthesis, the prosthesis including an implantable microstructure for stimulation of neural or glial tissue and for monitoring of neural function and a bi-directional interface coupled to the implantable microstructure, the bi-directional interface facilitating the transmission of at least one of stimulation and control signals from the encoder to the microstructure and of monitoring signals from the microstructure to the encoder, the encoder comprising:
    a central control unit performing signal processing functions, monitoring functions, control functions, and external pick-up functions, wherein the central control unit includes a group of adaptive spatio-temporal filters, the adaptive spatio-temporal filters converting sensory signals into stimulation pulse sequences.

14. The encoder according to claim 13, wherein the control unit includes in a perception-based dialog process receptive field (RF) filters, said RF filters comprising adjustable spatio-temporal filters with receptive field properties.

15. The encoder according to claim 14, wherein the RF filters are associated with time delay elements for a relative temporal sequence of impulse sequences produced.

16. The encoder according to claim 14, wherein a monitor is provided that displays imaging functions produced by the RF filters at least approximately inverted and optically or acoustically.

17. The encoder according to claim 13, further comprising:
a simulated eye movement system, the simulated eye movement system receiving input from head and eye movement detectors.

18. The encoder according to claim 13, wherein said central control unit controls a device for application of an active substance, the device being part of said implantable microstructure; and wherein the central control unit includes a monitoring system that receives indications of neural activity from said implantable microstructure via said monitoring signals.

19. The encoder according to claim 13, wherein said central control unit further comprises:
an adaptive pre-programming module, for simplification of image or sound patterns.

20. The encoder according to claim 13, wherein said central control unit includes at least one pattern recognition program.

21. A method for use with an adaptive sensory-motor encoder for a visual or acoustic prosthesis, the encoder comprising a central control unit performing signal processing functions, monitoring functions, control functions and external pick-up functions, as well as including a group of adaptive spatio-temporal filters, the prosthesis further including a microstructure for stimulation and monitoring of neural activity and a bi-directional interface coupling the encoder with the microstructure for transmission of at least one of control and stimulation signals from the encoder to the microstructure and of monitoring signals from the microstructure to the encoder, the method comprising the steps of:
supplying a minimum single-channel evaluation entry unit for individual adjustment of said signal processing functions by means of a dialog process, the evaluation entry unit using a subjective evaluation vector, where the evaluation vector represents similarity of a currently perceived pattern to a desired pattern;
transmitting the evaluation vector to a parameter adjustment system, to produce suitable sequences of parameter vectors, said parameter adjustment system comprising a neural network with non-monitored adaptation rules; and
generating, by said evaluation entry unit, a parameter vector at a multi-channel output for a respective signal processing function to be adjusted.

22. The method according to claim 21, wherein said signal processing functions comprise receptive field (RF) filters.

23. The method according to claim 22, further comprising the step of:
establishing, by the evaluation entry unit, appropriate pattern sequences for an adaptation process in a decision system for individual or group optimization of said RF filters.

24. The method according to claim 23, wherein said step of establishing comprises the step of:
generating internally stored sequences of parameter vectors for establishing typical RF filter functions.

25. The method according to claim 24, wherein said RF filters have a spatio-temporal function space that includes a function space of the receptive field properties of neurons at a site at which said microstructure is implanted.

26. The method according to claim 22, further comprising the steps of:
generating at least one signal by the RF filters;
emitting said at least one signal at said microstructure to elicit an actual perception; and
simultaneously passing an associated desired pattern to an output unit for perception by a human.

27. The method according to claim 26, wherein said microstructure includes a given number of micro-contacts, and further comprising the step of:
conducting, by an RF filter, said at least one signal to several locally adjacent micro-contacts for functionally increasing the number and definition of selectively reachable stimulation sites.

28. The method according to claim 26, wherein said at least one signal comprises at least two impulse signals, and further comprising the step of:
varying the at least two impulse signals for the purpose of shifting a focus of stimulation and varying stimulation sites.

29. The method according to claim 28, wherein said step of varying the at least two impulse signals comprises the step of:
effecting a perception-based dialog with a being in which the microstructure is implanted, for facilitating shifting of the stimulation focus so as to lead to selective and well-defined neural stimulation, the step of effecting a perception-based dialog including a step of utilizing optimization means in the central control unit.

30. The method according to claim 29, wherein said step of utilizing optimization means includes the step of utilizing a neural network.

31. The method according to claim 26, wherein said step of generating at least one signal comprises the step of generating at least one impulse signal.

32. The method according to claim 31, further comprising the steps of:
comparing recorded neural impulses to said at least one impulse signal;
distinguishing spontaneously occurring neural impulses from those produced in response to said at least one impulse signal; and
improving selectivity and biocompatibility of neural stimulation effected by said at least one impulse signal using results of said steps of comparing and distinguishing.

33. The method according to claim 21, further comprising the steps of:
detecting head movements and undesirable real eye movements;
simulating eye movements by means of at least one of electronic image pattern shifts, optical variation of direction of vision, and movement of photosensors;
using the detected head and real eye movements, as well as simulated eye movements produced by said step of simulating eye movements, by means of movement control or adjustment, quick and slow eye movements are produced for purposes of pattern recognition, tracking of moving objects, and fast circumspection.

34. The method of claim 33, further comprising the step of:
using said quick and slow eye movements to compensate for undesired eye movements or perceptions of apparent motion.

35. The method of claim 33, further comprising the step of:
generating compensatory eye movements with reference to the human vestibulo-ocular reflex for situational stabilization of an image pattern in the presence of normal head and upper body movements.

36. The method of claim 33, further comprising the step of:

facilitating technical adaptation of a brightness operating range resulting from a function range of a photosensor array extending over several brightness decades, said step of facilitating including the step of:
selecting an operating range for the encoder with respect to magnitude and adaptation brightness.

37. The method of claim 36, wherein said step of selecting an operating range comprises the steps of:

non-linearly evaluating sections of said function range; and composing said operating range from the resulting non-linearly evaluated sections of the function range.

38. The method of claim 37, further comprising the step of:

transposing visual scenes with local subsets of varying brightness into a common operating range of the encoder, using a suitable imaging system.

39. The method of claim 37, further comprising the step of:

if necessary, shifting RF filter functions for stimulation of perception a bright or dark adapted range using a brightness operating range of the encoder.

40. The method of claim 39, further comprising the step of:

rapidly changing the brightness operating range and the associated RF filter function shift automatically during simulated eye movements or during pattern recognition.

41. The method of claim 36, further comprising the steps of:

sharply adjusting first areas of a visual field by variation of accommodation;

storing the resulting sharply-adjusted first areas;

sharply adjusting, as an image, second areas of said visual field, whereby said initial areas become less sharp; and blending the stored sharply-adjusted first areas into the image in place of the first areas, which became less sharp in said step of sharply adjusting second areas.

42. The method of claim 36, wherein the method repeats itself cyclically.

43. The method of claim 21, further comprising the step of:

relaying a position of an object in space, determined by said encoder, to an appropriate sensory organ using a portable signal transmitter.

44. The method of claim 21, further comprising the steps of:

executing, in the encoder, at least one pattern recognition program, in connection with automatically running, simulated eye movements;

warning an implant carrier of obstacles or hazards detected based on results of said step of executing; and reporting a type and position of a technically identified pattern or object detected based on results of said step of executing.

* * * * *